United States Patent

Gesing et al.

(10) Patent No.: US 7,858,805 B2
(45) Date of Patent: Dec. 28, 2010

(54) SUBSTITUTED THIEN-3-YL-SULPHONYLAMINO(THIO)CARBONYL-TRIAZOLIN(ETHI)ONES

(75) Inventors: Ernst Rudolf F. Gesing, Leverkusen (DE); Joachim Kluth, Leverkusen (DE); Klaus-Helmut Müller, Leverkusen (DE); Mark Wilhelm Drewes, Leverkusen (DE); Peter Dahem, Leverkusen (DE); Dieter Feucht, Leverkusen (DE); Rolf Pontzen, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 12/614,001

(22) Filed: Nov. 6, 2009

(65) Prior Publication Data

US 2010/0056798 A1 Mar. 4, 2010

Related U.S. Application Data

(62) Division of application No. 11/044,969, filed on Jan. 27, 2005, which is a division of application No. 10/030,928, filed on Jan. 11, 2002, now Pat. No. 7,642,221.

(51) Int. Cl.
C07D 409/12 (2006.01)

(52) U.S. Cl. .................................. 548/263.4

(58) Field of Classification Search ........................ None
See application file for complete search history.

(56) References Cited

U.S. PATENT DOCUMENTS

| 4,180,662 A | 12/1979 | Pfister et al. |
| 4,701,535 A | 10/1987 | Levitt |
| 4,741,757 A | 5/1988 | Levitt |
| 5,149,356 A | 9/1992 | Muller et al. |
| 5,238,910 A | 8/1993 | Muller et al. |
| 5,241,074 A | 8/1993 | Daum et al. |
| 5,276,162 A | 1/1994 | Muller et al. |
| 5,300,480 A | 4/1994 | Haas et al. |
| 5,380,863 A | 1/1995 | Muller et al. |
| 5,380,864 A | 1/1995 | Muller et al. |
| 5,405,970 A | 4/1995 | Daum et al. |
| 5,488,028 A | 1/1996 | Haas et al. |
| 5,532,378 A | 7/1996 | Daum et al. |
| 5,534,486 A | 7/1996 | Muller et al. |
| 5,541,337 A | 7/1996 | Mueller et al. |
| 5,554,761 A | 9/1996 | Haas et al. |
| 5,597,939 A | 1/1997 | Muller et al. |
| 5,599,944 A | 2/1997 | Muller et al. |
| 5,625,074 A | 4/1997 | Daum et al. |
| 5,631,380 A | 5/1997 | Haas et al. |
| 5,652,372 A | 7/1997 | Muller et al. |
| 5,750,718 A | 5/1998 | Muller et al. |
| 5,869,681 A | 2/1999 | Muller et al. |
| 6,200,931 B1 | 3/2001 | Muller et al. |
| 6,518,222 B2 | 11/2003 | Arndt et al. |
| 6,645,918 B1 | 11/2003 | Arndt et al. |
| 2002/0094935 A1 | 7/2002 | Arndt et al. |
| 2003/0199393 A1 | 10/2003 | Arndt et al. |

FOREIGN PATENT DOCUMENTS

| EP | 0341489 | 11/1989 |
| EP | 0482349 | 4/1992 |
| WO | 9703980 | 2/1997 |
| WO | 9716449 | 5/1997 |
| WO | 9824787 | 6/1998 |

OTHER PUBLICATIONS

S.A. Henderson et al. "Activity of Crippled Biotin", Austr. J. Chem., 1995, 48, pp. 1907-1916, The Synthesis and Biological.
P.A. Rossy et al. "Thiophensaccharin: A Sweet Surprise", J. Org. Chem., 1980, 45, pp. 617-620, Aromatization of Dihydrothiophenes.

*Primary Examiner*—Kamal A Saeed
(74) *Attorney, Agent, or Firm*—Baker Donelson Bearman, Caldwell & Berkowitz, PC

(57) ABSTRACT

The invention relates to processes for the preparation of compounds of general formula (I) and salts thereof:

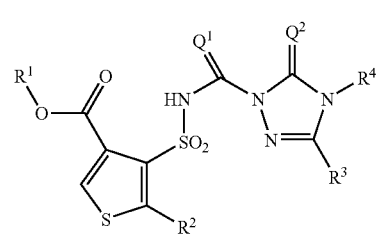

in which
$Q^1$ represents O,
$Q^2$ represents O,
$R^1$ represents —$CH_3$,
$R^2$ represents —$CH_3$,
$R^3$ represents —$OCH_3$, and
$R^4$ represents —$CH_3$.

2 Claims, No Drawings

SUBSTITUTED THIEN-3-YL-SULPHONYLAMINO(THIO)CARBONYL-TRIAZOLIN(ETHI)ONES

CROSS-REFERENCE TO RELATED APPLICATIONS

This is a divisional of U.S. patent application Ser. No. 11/044,969, filed Jan. 27, 2005, which is a divisional of U.S. patent application Ser. No. 10/030,928 filed Jan. 1, 2002, now U.S. Pat. No. 6,964,939, which is the U.S. national stage of PCT Application Serial No. PCT/EP00/06276, filed Jul. 4, 2000, which in turn claims priority to German Patent Application No. 199 33 260.6, filed Jul. 15, 1999.

The invention relates to novel substituted thien-3-yl-sulphonylamino(thio)carbonyl-triazolin(ethi)ones, to processes and novel intermediates for their preparation and to their use as herbicides.

It is already known that certain substituted thienylsulphonylamino(thio)carbonyl-triazolin(ethi)ones have herbicidal properties (cf. WO-A-97/16449, WO-A-98/24787). However, the activity of these compounds is not entirely satisfactory.

This invention, accordingly, provides the novel substituted thien-3-yl-sulphonylamino-(thio)carbonyl-triazolin(ethi)ones of the general formula (I)

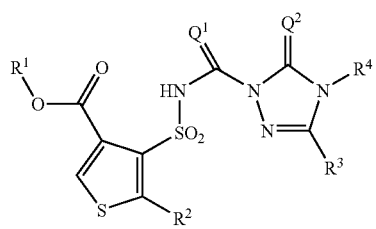

(I)

in which
$Q^1$ represents O (oxygen) or S (sulphur),
$Q^2$ represents O (oxygen) or S (sulphur),
$R^1$ represents in each case optionally substituted alkyl, alkenyl, alkinyl, cycloalkyl, cycloalkylalkyl, aryl, arylalkyl, heterocyclyl or heterocyclylalkyl,
$R^2$ represents hydrogen, cyano, nitro, halogen or represents in each case optionally substituted alkyl, alkoxy, alkoxycarbonyl, alkylthio, alkylsulphinyl, alkylsulphonyl, alkenyl, alkinyl, alkenyloxy or alkinyloxy,
$R^3$ represents hydrogen, hydroxyl, mercapto, amino, cyano, halogen or represents in each case optionally substituted alkyl, alkenyl, alkinyl, alkoxy, alkylthio, alkylamino, alkylcarbonylamino, alkenyloxy, alkinyloxy, alkenylthio, alkinylthio, alkenylamino, alkinylamino, dialkylamino, aziridino, pyrrolidino, piperidino, morpholino, cycloalkyl, cycloalkenyl, cycloalkyloxy, cycloalkylthio, cycloalkylamino, cycloalkylalkyl, cycloalkylalkoxy, cycloalkylalkylthio, cycloalkylalkylamino, aryl, arylalkyl, aryloxy, arylalkoxy, arylthio, arylalkylthio, arylamino or arylalkylamino, and
$R^4$ represents hydrogen, hydroxyl, amino, cyano, represents alkylideneamino or represents in each case optionally substituted alkyl, alkenyl, alkinyl, alkoxy, alkylamino, alkylcarbonylamino, alkenyloxy, dialkylamino, cycloalkyl, cycloalkylamino, cycloalkylalkyl, aryl or arylalkyl, or
$R^3$ and $R^4$ together represent optionally branched alkanediyl,
—and salts of the compounds of the formula (I)—.

Saturated or unsaturated hydrocarbon groupings, such as alkyl, alkanediyl, alkenyl or alkinyl, are in each case straight-chain or branched as far as this is possible—including in combination with heteroatoms, such as in alkoxy.

Optionally substituted radicals can be mono- or polysubstituted, where, in the case of polysubstitution, the substituents can be identical or different.

Preferred substituents or ranges of the radicals present in the formulae given above and below are defined below.

$Q^1$ preferably represents O (oxygen) or S (sulphur).
$Q^2$ preferably represents O (oxygen) or S (sulphur).
$R^1$ preferably represents optionally cyano-, halogen- or $C_1$-$C_4$-alkoxy-substituted alkyl having 1 to 6 carbon atoms, represents in each case optionally cyano- or halogen-substituted alkenyl or alkinyl having in each case 2 to 6 carbon atoms, represents in each case optionally cyano-, halogen- or $C_1$-$C_4$-alkyl-substituted cycloalkyl or cycloalkylalkyl having in each case 3 to 6 carbon atoms in the cycloalkyl group and optionally 1 to 4 carbon atoms in the alkyl moiety, represents in each case optionally nitro-, cyano-, halogen-, $C_1$-$C_4$-alkyl- or $C_1$-$C_4$-alkoxy-substituted aryl or arylalkyl having in each case 6 or 10 carbon atoms in the aryl group and optionally 1 to 4 carbon atoms in the alkyl moiety, or represents in each case optionally nitro-, cyano-, halogen-, $C_1$-$C_4$-alkyl- or $C_1$-$C_4$-alkoxy-substituted heterocyclyl or heterocyclylalkyl having in each case up to 6 carbon atoms and additionally 1 to 4 nitrogen atoms and/or 1 to 2 oxygen or sulphur atoms in the heterocyclyl group and optionally 1 to 4 carbon atoms in the alkyl moiety.

$R^2$ preferably represents hydrogen, cyano, nitro, halogen, represents in each case optionally cyano-, halogen- or $C_1$-$C_4$-alkoxy-substituted alkyl, alkoxy, alkoxy-carbonyl, alkylthio, alkylsulphinyl or alkylsulphonyl having in each case 1 to 6 carbon atoms in the alkyl group, or represents in each case optionally cyano- or halogen-substituted alkenyl, alkinyl, alkenyloxy or alkinyloxy having in each case 2 to 6 carbon atoms in the alkenyl or alkinyl group.

$R^3$ preferably represents hydrogen, hydroxyl, mercapto, amino, cyano, fluorine, chlorine, bromine, iodine, represents optionally fluorine-, chlorine-, bromine-, cyano-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, represents in each case optionally fluorine-, chlorine- and/or bromine-substituted alkenyl or alkinyl having in each case 2 to 6 carbon atoms, represents in each case optionally fluorine-, chlorine-, cyano-, $C_1$-$C_4$-alkoxy- or $C_1$-$C_4$-alkoxy-carbonyl-substituted alkoxy, alkylthio, alkylamino or alkylcarbonylamino having in each case 1 to 6 carbon atoms in the alkyl group, represents alkenyloxy, alkinyloxy, alkenylthio, alkinylthio, alkenylamino or alkinylamino having in each case 3 to 6 carbon atoms in the alkenyl or alkinyl group, represents dialkylamino having in each case 1 to 4 carbon atoms in the alkyl groups, represents in each case optionally methyl- and/or ethyl-substituted aziridino, pyrrolidino, piperidino or morpholino, represents in each case optionally fluorine-, chlorine-, bromine-, cyano- and/or $C_1$-$C_4$-alkyl-substituted cycloalkyl, cycloalkenyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl or cycloalkenyl group and optionally 1 to 4 carbon atoms in the alkyl moiety, or represents in each case optionally fluorine-, chlorine-, bromine-, cyano-, nitro-, $C_1$-$C_4$-alkyl-, trifluoromethyl-, $C_1$-$C_4$-alkoxy- and/or $C_1$-$C_4$-alkoxy-carbonyl-substituted aryl, arylalkyl, aryloxy, arylalkoxy, arylthio, arylalkylthio, arylamino or arylalkylamino having in each case 6 or 10 carbon atoms in the aryl group and optionally 1 to 4 carbon atoms in the alkyl moiety.

$R^4$ preferably represents hydrogen, hydroxyl, amino, cyano, represents $C_2$-$C_{10}$-alkylideneamino, represents optionally fluorine-, chlorine-, bromine-, cyano-, $C_1$-$C_4$-alkoxy-, $C_1$-$C_4$-alkyl-carbonyl- or $C_1$-$C_4$-alkoxy-carbonyl-substituted alkyl having 1 to 6 carbon atoms, represents in each case optionally fluorine-, chlorine- and/or bromine-substituted alkenyl or alkinyl having in each case 2 to 6 carbon atoms, represents in each case optionally fluorine-, chlorine-, bromine-, cyano-, $C_1$-$C_4$-alkoxy- or $C_1$-$C_4$-alkoxycarbonyl-substituted alkoxy, alkylamino or alkylcarbonylamino having in each case 1 to 6 carbon atoms in the alkyl group, represents alkenyloxy having 3 to 6 carbon atoms, represents dialkylamino having in each case 1 to 4 carbon atoms in the alkyl groups, represents in each case optionally fluorine-, chlorine-, bromine-, cyano- and/or $C_1$-$C_4$-alkyl-substituted cycloalkyl, cycloalkylamino or cycloalkylalkyl having in each case 3 to 6 carbon atoms in the alkyl group and optionally 1 to 4 carbon atoms in the alkyl moiety, or represents in each case optionally fluorine-, chlorine-, bromine-, cyano-, nitro-, $C_1$-$C_4$-alkyl-, trifluoromethyl- and/or $C_1$-$C_4$-alkoxy-substituted aryl or arylalkyl having in each case 6 or 10 carbon atoms in the aryl group and optionally 1 to 4 carbon atoms in the alkyl moiety.

$R^3$ and $R^4$ together also preferably represent optionally branched alkanediyl having 3 to 6 carbon atoms.

$Q^1$ particularly preferably represents O (oxygen) or S (sulphur).

$Q^2$ particularly preferably represents O (oxygen) or S (sulphur).

$R^1$ particularly preferably represents in each case optionally cyano-, fluorine-, chlorine-, methoxy- or ethoxy-substituted methyl, ethyl, n- or i-propyl, n-, i-, s- or t-butyl, represents in each case optionally cyano-, fluorine- or chlorine-substituted propenyl, butenyl, propinyl or butinyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, represents in each case optionally cyano-, fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenyl, phenylmethyl or phenylethyl, or represents in each case optionally cyano-, fluorine-, chlorine-, bromine-, methyl-, ethyl-, n- or i-propyl-, methoxy-, ethoxy-, n- or i-propoxy-substituted heterocyclyl or heterocyclylmethyl, where the heterocyclyl group is in each case selected from the group consisting of oxetanyl, thietanyl, furyl, tetrahydrofuryl, thienyl, tetrahydrothienyl.

$R^2$ particularly preferably represents hydrogen, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl, or represents in each case optionally cyano-, fluorine- or chlorine-substituted propenyl, butenyl, propinyl, butinyl, propenyloxy, butenyloxy, propinyloxy or butinyloxy.

$R^3$ particularly preferably represents hydrogen, hydroxyl, mercapto, amino, cyano, fluorine, chlorine, bromine, represents in each case optionally fluorine-, chlorine-, cyano-, methoxy-, ethoxy-, n- or i-propoxy, acetyl-, propionyl-, n- or i-butyroyl-, methoxycarbonyl-, ethoxycarbonyl-, n- or i-propoxycarbonyl-substituted methyl, ethyl, n- or i-propyl, n-, i-, s- or t-butyl, represents in each case optionally fluorine-, chlorine- and/or bromine-substituted ethenyl, propenyl, butenyl, ethinyl, propinyl or butinyl, represents in each case optionally fluorine-, chlorine-, cyano-, methoxy-, ethoxy-, n- or i-propoxy-, methoxycarbonyl-, ethoxycarbonyl-, n- or i-propoxycarbonyl-substituted methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, acetylamino or propionylamino, represents propenyloxy, butenyloxy, ethinyloxy, propinyloxy, butinyloxy, propenylthio, butenylthio, propinylthio, butinylthio, propenylamino, butenylamino, propinylamino or butinylamino, represents dimethylamino, diethylamino or dipropylamino, represents in each case optionally fluorine-, chlorine-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, bromine-, methyl-, trifluoromethyl-, methoxy- or methoxycarbonyl-substituted phenyl, benzyl, phenoxy, benzyloxy, phenylthio, benzylthio, phenylamino or benzylamino.

$R^4$ particularly preferably represents hydrogen, hydroxyl, amino, represents in each case optionally fluorine-, chlorine-, cyano-, methoxy- or ethoxy-substituted methyl, ethyl, n- or i-propyl, n-, i-, s- or t-butyl, represents in each case optionally fluorine-, chlorine- and/or bromine-substituted ethenyl, propenyl, butenyl, propinyl or butinyl, represents in each case optionally fluorine-, chlorine-, cyano-, methoxy- or ethoxy-substituted methoxy, ethoxy, n- or i-propoxy, n-, i-, s- or t-butoxy, methylamino, ethylamino, n- or i-propylamino, n-, i-, s- or t-butylamino, represents propenyloxy or butenyloxy, represents dimethylamino or diethylamino, represents in each case optionally fluorine-, chlorine-, methyl- and/or ethyl-substituted cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, or represents in each case optionally fluorine-, chlorine-, methyl-, trifluoromethyl- and/or methoxy-substituted phenyl or benzyl.

$R^3$ and $R^4$ together also particularly preferably represent trimethylene (propan-1,3-diyl), tetramethylene (butan-1,4-diyl) or pentamethylene (pentane-1,5-diyl).

$Q^1$ very particularly preferably represents O (oxygen).

$Q^2$ very particularly preferably represents O (oxygen).

$R^1$ very particularly preferably represents in each case optionally fluorine-, chlorine-, methoxy- or ethoxy-substituted methyl, ethyl, n- or i-propyl.

$R^2$ very particularly preferably represents fluorine, chlorine, bromine or represents in each case optionally fluorine-, chlorine-, methoxy- or ethoxy-substituted methyl, ethyl, n- or i-propyl.

$R^3$ very particularly preferably represents hydrogen, chlorine, bromine, represents in each case optionally fluorine-, chlorine-, methoxy-, ethoxy-, n- or i-propoxy-substituted methyl, ethyl, n- or i-propyl, represents in each case optionally fluorine- or chlorine-substituted ethenyl, propenyl, butenyl, propinyl or butinyl, represents in each case optionally fluorine-, chlorine-, methoxy-, ethoxy-, n- or i-propoxy-substituted methoxy, ethoxy, n- or i-propoxy, methylthio, ethylthio, n- or i-propylthio, methylamino, ethylamino, n- or i-propylamino, represents propenyloxy, propinyloxy, propenylthio, propinylthio, propenylamino or propinylamino, represents dimethylamino or diethylamino, represents in each case optionally fluorine-, chlorine- or methyl-substituted cyclopropyl, cyclopropyloxy, cyclopropylmethyl or cyclopropylmethoxy.

$R^4$ very particularly preferably represents in each case optionally fluorine-, chlorine-, methoxy- or ethoxy-substituted methyl, ethyl, n- or i-propyl, represents in each case optionally fluorine- or chlorine-substituted ethenyl, propenyl or propinyl, represents in each case optionally fluorine-, chlorine-, methoxy- or ethoxy-substituted methoxy, ethoxy, n- or i-propoxy, represents methylamino, or represents cyclopropyl.

$R^1$ most preferably represents methyl, ethyl, n- or i-propyl.

$R^2$ most preferably represents methyl, ethyl, n- or i-propyl.

$R^3$ most preferably represents methoxy, ethoxy, n- or i-propoxy, methyl, ethyl, n- or i-propyl, methylthio, ethylthio, n- or i-propylthio or cyclopropyl.

$R^4$ most preferably represents methyl, ethyl, n- or i-propyl or cyclopropyl.

The invention also preferably provides the sodium, potassium, magnesium, calcium, ammonium, $C_1$-$C_4$-alkyl-ammonium-, di-($C_1$-$C_4$-alkyl)-ammonium, tri-($C_1$-$C_4$-alkyl)-ammonium, tetra-($C_1$-$C_4$-alkyl)-ammonium, tri-($C_1$-$C_4$-alkyl)-sulphonium, $C_5$- or $C_6$-cycloalkyl-ammonium and di-($C_1$-$C_2$-alkyl)-benzyl-ammonium salts of compounds of the formula (I) in which $Q^1$, $Q^2$, $R^1$, $R^2$, $R^3$ and $R^4$ each preferably have the meanings given above.

The abovementioned general or preferred radical definitions apply both to the end products of the formula (I) and, correspondingly, to the starting materials or intermediates required in each case for the preparation. These radical definitions can be combined with one another as desired, i.e. including combinations between the given preferred ranges.

Preference according to the invention is given to those compounds of the formula (I) which contain a combination of the meanings listed above as being preferred.

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

The novel substituted thien-3-yl-sulphonylamino(thio)carbonyl-triazolin(ethi)ones of the general formula (I) have interesting biological properties. In particular, they have strong herbicidal activity.

The novel substituted thien-3-yl-sulphonylamino(thio)carbonyl-triazolin(ethi)ones of the general formula (I) are obtained when (a) Substituted Thiophene-3-Sulphonamides of the General Formula (II)

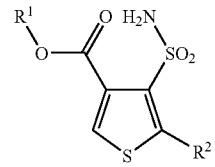

in which $R^1$ and $R^2$ are each as defined above, are reacted with substituted triazolin(ethi)ones of the general formula (III)

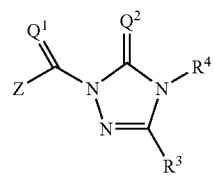

in which $Q^1$, $Q^2$, $R^3$ and $R^4$ are each as defined above and

Z represents halogen, alkoxy, aryloxy or arylalkoxy, if appropriate in the presence of a reaction auxiliary and if appropriate in the presence of a diluent, or when (b) Substituted Thien-3-yl-Sulphonyl Iso(Thio)Cyanates of the General Formula (IV)

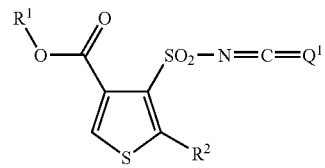

in which $Q^1$, $R^1$ and $R^2$ are each as defined above, are reacted with triazolin(ethi)ones of the general formula (V)

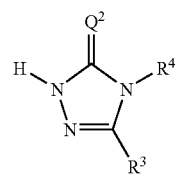

in which $Q^2$, $R^3$ and $R^4$ are each as defined above, if appropriate in the presence of a reaction auxiliary and if appropriate in the presence of a diluent, or when (c) Substituted Thiophene-3-Sulphonyl Chlorides of the General Formula (VI)

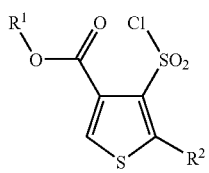
(VI)

in which

R¹ and R² are each as defined above, are reacted with triazolin(ethi)ones of the general formula (V)

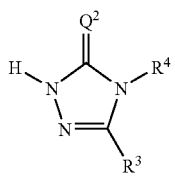
(V)

in which

Q², R³ and R⁴ are each as defined above, and metal (thio)cyanates of the general formula (VII)

 (VII)

in which

Q¹ is as defined above, if appropriate in the presence of a reaction auxiliary and if appropriate in the presence of a diluent, or when (d) substituted thiophene-3-sulphonyl chlorides of the general formula (VI)

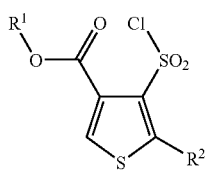
(VI)

in which

R¹ and R² are each as defined above, are reacted with triazolin(ethi)one-(thio)carboxamides of the general formula (VIII)

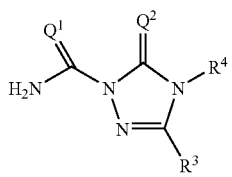
(VIII)

in which

Q¹, Q², R³ K and R⁴ are each as defined above, if appropriate in the presence of a reaction auxiliary and if appropriate in the presence of a diluent, or when (e) substituted thien-3-yl-sulphonylamino(thio)carbonyl compounds of the general formula (IX)

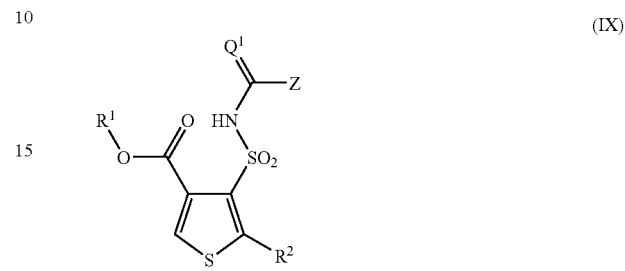
(IX)

in which

Q¹, R¹ and R² are each as defined above and

Z represents halogen, alkoxy, aryloxy or arylalkoxy, are reacted with triazolin(ethi)ones of the general formula (V)

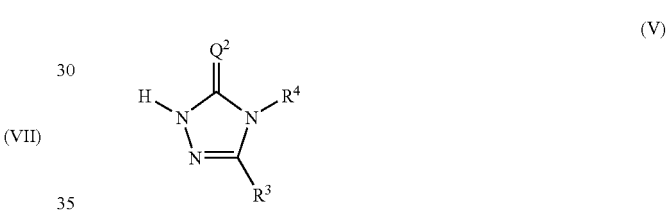
(V)

in which

Q², R³ and R⁴ are each as defined above, if appropriate in the presence of a reaction auxiliary and if appropriate in the presence of a diluent, and the compounds of the formula (I) obtained by the processes (a), (b), (c), (d) or (e) are, if appropriate, converted by customary methods into salts.

Using, for example, 2-chloro-4-ethoxycarbonyl-thiophene-3-sulphonamide and 4,5-dimethoxy-2-phenoxy-carbonyl-2,4-dihydro-3H-1,2,4-triazol-3-one as starting materials, the course of the reaction in the process (a) according to the invention can be illustrated by the following formula scheme:

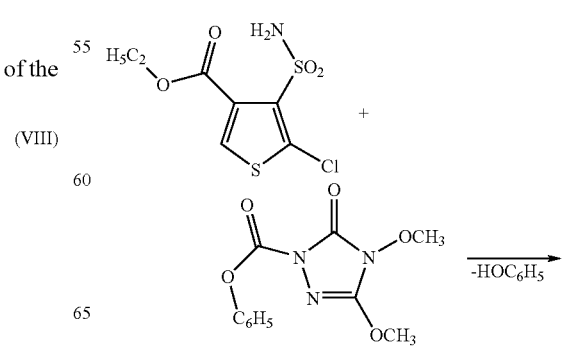

-continued

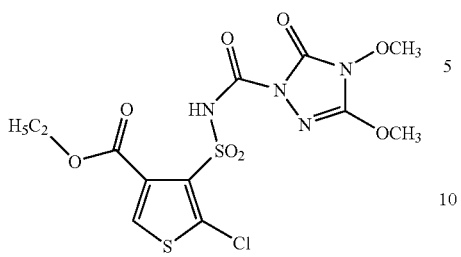

Using, for example, 2-fluoro-4-methoxycarbonyl-thien-3-yl-sulphonyl isothiocyanate and 5-ethoxy-4-methyl-2,4-dihydro-3H-1,2,4-triazol-3-one as starting materials, the course of the reaction in the process (b) according to the invention can be illustrated by the following formula scheme:

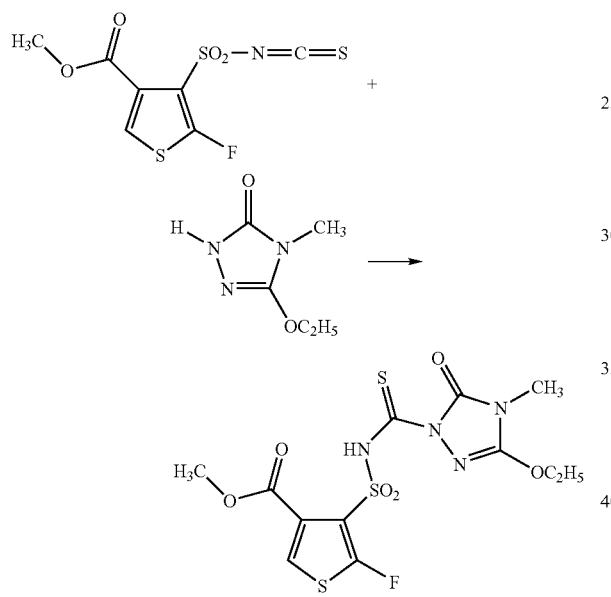

Using, for example, 4-methoxycarbonyl-2-trifluoromethyl-thiophene-3-sulphonyl chloride, 5-ethyl-4-methoxy-2,4-dihydro-3H-1,2,4-triazol-3-thione and potassium cyanate as starting materials, the course of the reaction in the process (c) according to the invention can be illustrated by the following formula scheme:

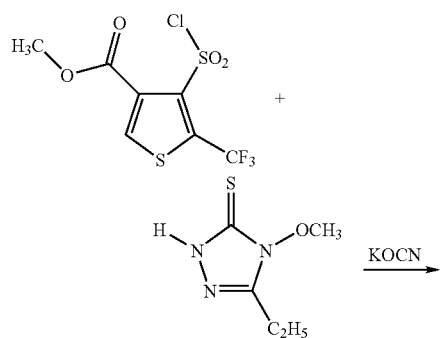

-continued

Using, for example, 3-ethoxycarbonyl-2-methyl-thiophene-4-sulphonyl chloride and 4-ethyl-5-methoxy-2,4-dihydro-3H-1,2,4-triazol-3-one-2-carboxamide as starting materials, the course of the reaction in the process (d) according to the invention can be illustrated by the following formula scheme:

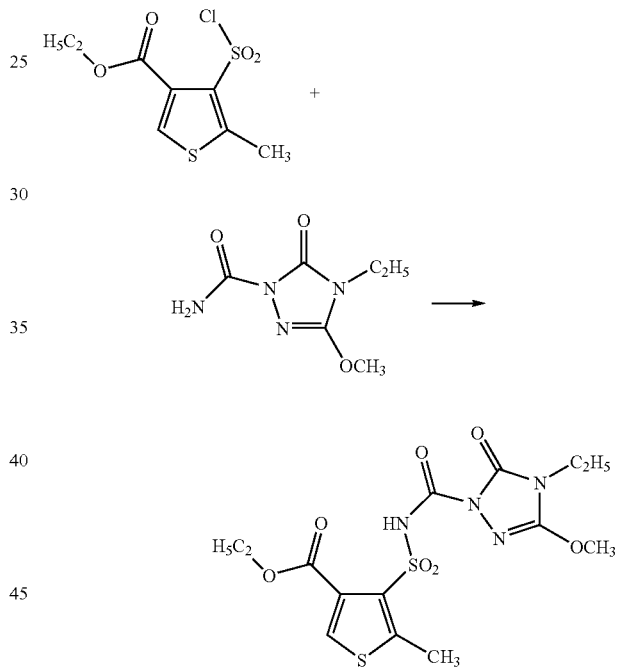

Using, for example, O-methyl N-(2-ethyl-4-i-propoxycarbonyl-thien-3-yl-sulphonyl)-urethane and 4,5-dimethyl-2,4-dihydro-3H-1,2,4-triazol-3-one as starting materials, the course of the reaction in the process (e) according to the invention can be illustrated by the following formula scheme:

-continued

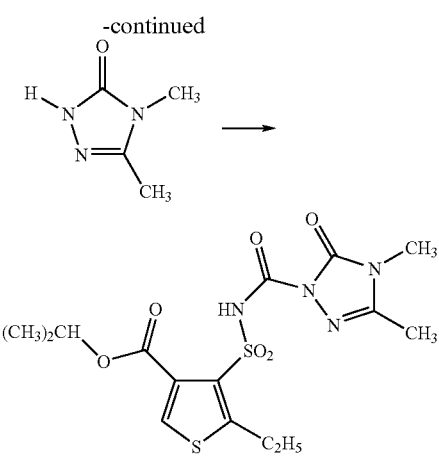

The formula (II) provides a general definition of the substituted thiophene-3-sulphonamides to be used as starting materials in the process (a) according to the invention for preparing compounds of the general formula (I). In the general formula (II), $R^1$ and $R^2$ each preferably have those meanings which have already been mentioned above, in connection with the description of the compounds of the general formula (I) according to the invention, as being preferred, or those which have been mentioned in one of the particularly preferred definitions for $R^1$ and $R^2$.

Except for 4-methoxycarbonyl-thiophene-3-sulphonamide (cf. J. Org. Chem. 45 (1980), 617-620), the substituted thiophene-3-sulphonamides of the general formula (II) have hitherto not been disclosed in the literature; except for 4-methoxycarbonyl-thiophene-3-sulphonamide, they also form, as novel substances, part of the subject-matter of the present application.

The substituted thiophene-3-sulphonamides of the general formula (II) are obtained when substituted thiophene-3-sulphonyl chlorides of the general formula (VI)

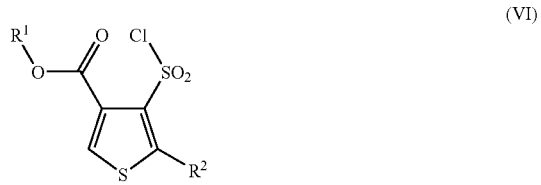

in which $R^1$ and $R^2$ are each as defined above, are reacted with ammonia or ammonium salts, such as, for example, ammonium acetate or ammonium carbonate, if appropriate in the presence of a diluent, such as, for example, water or methylene chloride, at temperatures between 0° C. and 100° C. (cf. the Preparation Examples).

The formula (III) provides a general definition of the substituted triazolin(ethi)ones furthermore to be used as starting materials in the process (a) according to the invention for preparing compounds of the general formula (I). In the general formula (III), $Q^1$, $Q^2$, $R^3$ and $R^4$ each preferably have those meanings which have already been mentioned above, in connection with the description of the compounds of the general formula (I) according to the invention, as being preferred, or those which have been mentioned in one of the particularly preferred definitions for $Q^1$, $Q^2$, $R^3$ and $R^4$.

The starting materials of the general formula (III) are known and/or can be prepared by processes known per se (cf. EP-A-341 489, EP-A-422 469, EP-A-425 948, EP-A-431 291, EP-A-507 171, EP-A-534 266).

The formula (IV) provides a general definition of the substituted thien-3-yl-sulphonyl iso(thio)cyanates to be used as starting materials in the process (b) according to the invention for preparing compounds of the general formula (I). In the general formula (IV), $Q^1$, $R^1$ and $R^2$ each preferably have those meanings which have already been mentioned above, in connection with the description of the compounds of the general formula (I) according to the invention, as being preferred, or those which have been mentioned in one of the particularly preferred definitions for $Q^1$, $R^1$ and $R^2$.

The starting materials of the general formula (IV) are known and/or can be prepared by processes known per se (cf. U.S. Pat. No. 4,701,535).

The formula (V) provides a general definition of the triazolin(ethi)ones to be used as starting materials in the processes (b), (c) and (e) according to the invention for preparing compounds of the general formula (I). In the general formula (V), $Q^2$, $R^4$ and $R^5$ each preferably have those meanings which have already been mentioned above, in connection with the description of the compounds of the general formula (I) according to the invention, as being preferred, or those which have been mentioned in one of the particularly preferred definitions of $Q^2$, $R^4$ and $R^5$.

The starting materials of the general formula (V) are known and/or can be prepared by processes known per se (cf. EP-A-341 489, EP-A-422 469, EP-A-425 948, EP-A-431 291, EP-A-507 171, EP-A-534 266).

The formula (VI) provides a general definition of the substituted thiophene-3-sulphonyl chlorides to be used as starting materials in the processes (c) and (d) according to the invention for preparing compounds of the general formula (I). In the general formula (VI), $R^1$ and $R^2$ each preferably have those meanings which have already been mentioned above, in connection with the description of the compounds of the general formula (I) according to the invention, as being preferred, or those which have been mentioned in one of the particularly preferred definitions of $R^1$ and $R^2$.

Except for 4-methoxycarbonyl-thiophene-3-sulphonyl chloride (cf. J. Org. Chem. 45 (1980), 617-620), the substituted thiophene-3-sulphonyl chlorides of the general formula (VI) have hitherto not been disclosed in the literature; except for 4-methoxycarbonyl-thiophen-3-sulphonyl chloride, they also form, as novel substances, part of the subject-matter of the present application.

The substituted thiophene-3-sulphonyl chlorides of the general formula (VI) are obtained when 3-amino-thiophene-4-carboxylic esters of the general formula (X)

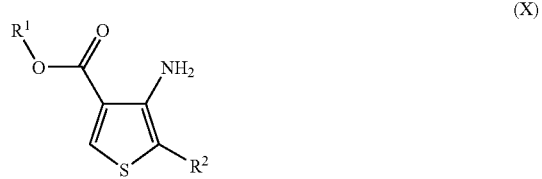

in which $R^1$ and $R^2$ are each as defined above,

—or acid adducts of compounds of the formula (X), such as, for example, the hydrochlorides— are reacted with an alkali metal nitrite, such as, for example, sodium nitrite, in the presence of hydrochloric acid at temperatures between −10° C. and +10° C., and the resulting diazonium salt solution is reacted with sulphur dioxide in the presence of a diluent, such as, for example, dichloromethane, 1,2-dichloro-ethane or acetic acid, and in the presence of a catalyst, such as, for example, copper(I) chloride and/or copper(II) chloride, at temperatures between −10° C. and +50° C.

The intermediates of the general formula (X) are known and/or can be prepared by processes known per se (cf. Austr. J. Chem. 48 (1995), 1907-1916; Preparation Examples).

The formula (VIII) provides a general definition of the triazolin(ethi)one-(thio)carboxamides to be used as starting materials in the process (d) according to the invention for preparing compounds of the general formula (I). In the general formula (VIII), $Q^1$, $Q^2$, $R^3$ and $R^4$ each preferably have those meanings which have already been mentioned above, in connection with the description of the compounds of the general formula (I) according to the invention, as being preferred, or those which have been mentioned in one of the particularly preferred definitions for $Q^1$, $Q^2$, $R^3$ and $R^4$.

The starting materials of the general formula (VIII) are known and/or can be prepared by processes known per se.

The formula (IX) provides a general definition of the substituted thien-3-yl-sulphonylamino(thio)carbonyl compounds to be used as starting materials in the process (e) according to the invention for preparing compounds of the general formula (I). In the general formula (IX), $Q^1$, $R^1$ and $R^2$ each preferably have those meanings which have already been mentioned above, in connection with the description of the compounds of the general formula (I) according to the invention, as being preferred, or those which have been mentioned in one of the particularly preferred definitions for $Q^1$, $R^1$ and $R^2$. The starting materials of the general formula (IX) are known and/or can be prepared by processes known per se.

The processes (a), (b), (c), (d) and (e) according to the invention for preparing the novel compounds of the formula (I) are preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethyl phosphoric triamide.

Reaction auxiliaries suitable for the processes (a), (b), (c), (d) and (e) according to the invention are all acid binders which are customarily used for such reactions. Preference is given to alkali metal hydroxides, such as, for example, sodium hydroxide and potassium hydroxide, alkaline earth metal hydroxides, such as, for example, calcium hydroxide, alkali metal carbonates and alkoxides, such as sodium carbonate and potassium carbonate, sodium tert-butoxide and potassium tert-butoxide, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4.3.0]-non-5-ene (DBN), 1,8-diazabicyclo-[5.4.0]-undec-7-ene (DBU) and 1,4-diazabicyclo[2.2.2]-octane (DABCO).

The reaction temperatures in the processes (a), (b), (c), (d) and (e) according to the invention can be varied within a relatively wide range. In general, the processes are carried out at temperatures between −20° C. and +150° C., preferably at temperatures between 0° C. and +100° C.

The processes (a), (b), (c), (d) and (e) according to the invention are generally carried out under atmospheric pressure. However, it is also possible to operate under elevated or reduced pressure.

For carrying out the processes (a), (b), (c), (d) and (e) according to the invention, the starting materials required in each case are generally employed in approximately equimolar amounts. However, it is also possible to use a relatively large excess of one of the components used in each case. The reactions are generally carried out in a suitable diluent in the presence of an acid acceptor, and the reaction mixture is stirred for several hours at the temperature required in each case. Work-up in the processes (a), (b), (c), (d) and (e) according to the invention is in each case carried out by customary methods (cf. the Preparation Examples).

If appropriate, salts can be prepared from the compounds of the general formula (I) according to the invention. Such salts are obtained in a simple manner by customary methods for forming salts, for example by dissolving or dispersing a compound of the formula (I) in a suitable solvent, such as, for example, methylene chloride, acetone, tert-butyl methyl ether or toluene, and adding a suitable base. The salts can then—if appropriate after prolonged stirring—be isolated by concentration or filtration with suction.

The active compounds according to the invention can be used as defoliants, desiccants, haulm killers and, especially, as weedkillers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

According to the invention, it is possible to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including transgenic plants and including plant varieties which may or may not be protectable by plant variety property rights. Parts of plants are to be understood as meaning all above-ground and below-ground parts and organs of plants, such as shoot, leaf, flower and root, examples which may be mentioned being leaves, needles, stems, trunks, flowers, shoot-bodies, fruits and seeds and also roots, and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation materials, in particular in the case of seeds, furthermore by single- or multi-layer coating.

Depending on the concentration, the active compounds according to the invention are suitable for total weed control, for example on industrial sites and rail tracks and on paths and areas with or without tree growth. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when applied on the soil and on above-ground parts of plants. To a certain extent, they are also suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzobicyclon, benzolenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlorotoluron, cinidon(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysulfuron, etobenzanid, fenoxaprop-(-P-ethyl), fentrazamide, flamprop(-isopropyl), flamprop(-isopropyl-L), flamprop(-methyl), flazasulfuron, florasulam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluoroxypyr(-methyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, terbuthylazine, terbutryn, thenylchlor, thiafluamide, thiazopyr, thidiazimin, thifen-sulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

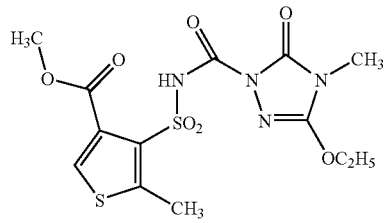

(Process (a))

0.76 g (2.9 mmol) of 5-ethoxy-4-methyl-2-phenoxycarbonyl-2,4-dihydro-3H-1,2,4-triazol-3-one are dissolved in 40 ml of acetonitrile and, at room temperature (about 20° C.) admixed a little at a time and with stirring with 0.75 g (3.2 mmol) of 4-methoxycarbonyl-2-methyl-thiophene-3-sulphonamide and 0.49 g (3.2 mmol) of 1,8-diazabicyclo-[5.4.0]-undec-7-ene (DBU). The reaction mixture is stirred at room temperature for 12 hours and then concentrated under reduced pressure. The residue is taken up in methylene chloride, washed successively with 1 N hydrochloric acid and water, dried with sodium sulphate and filtered. The filtrate is concentrated under water pump vacuum, the residue is digested with isopropanol and the resulting crystalline product is isolated by filtration with suction.

This gives 0.70 g (60% of theory) of methyl 4-[[[(3-ethoxy-4,5-dihydro-4-methyl-5-oxo-1H-1,2,4-triazol-1-yl)-carbonyl]-amino]-sulphonyl]-5-methyl-thiophene-3-carboxylate (alias 5-ethoxy-4-methyl-2-[(4-methoxycarbonyl-2-methyl-thien-3-yl)-sulphonyl-amino-carbonyl]-2,4-dihydro-3H-1,2,4-triazol-3-one) of melting point 163° C.

Analogously to Example 1, and in accordance with the general description of the preparation processes according to the invention, it is also possible to prepare, for example, the compounds of the general formula (I) listed in Table 1 below.

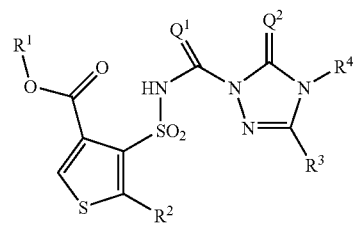

(I)

TABLE 1

Examples of compounds of the formula (I)

| Ex. No. | $Q^1$ | $Q^2$ | $R^1$ | $R^2$ | $R^3$ | $R^4$ | Melting point (° C.) |
|---|---|---|---|---|---|---|---|
| 2 | O | O | $CH_3$ | $CH_3$ | $OCH_3$ | $CH_3$ | 201 |
| 3 | O | O | $CH_3$ | $CH_3$ | $OC_3H_7$-n | $CH_3$ | 156 |
| 4 | O | O | $CH_3$ | $CH_3$ | $OC_3H_7$-i | $CH_3$ | 150 |
| 5 | O | O | $CH_3$ | $CH_3$ | $OCH_3$ | △ | 218 |
| 6 | O | O | $CH_3$ | $CH_3$ | $OC_2H_5$ | △ | 170 |
| 7 | O | O | $CH_3$ | $CH_3$ | $OC_3H_7$-n | △ | 156 |
| 8 | O | O | $CH_3$ | $CH_3$ | $OC_3H_7$-i | △ | 188 |
| 9 | O | O | $CH_3$ | $CH_3$ | △ | △ | 200 |
| 10 | O | O | $CH_3$ | $CH_3$ | $CH_3$ | $CH_3$ | 178 |
| 11 | O | O | $CH_3$ | $CH_3$ | $C_2H_5$ | $CH_3$ | 161 |
| 12 | O | O | $CH_3$ | $CH_3$ | $SCH_3$ | $CH_3$ | 183 |

Starting Materials of the Formula (II)

Example (II-1)

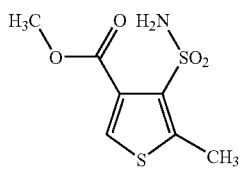

A mixture of 45 g (177 mmol) of 4-methoxycarbonyl-2-methyl-thiophene-3-sulphonyl chloride, 34 g (354 mmol) of ammonium carbonate and 400 ml of methylene chloride is stirred at room temperature (about 20° C.) for 12 hours. The mixture is filtered and the solvent is then distilled off from the filtrate under water pump vacuum, the residue is digested with diethyl ether and the crystalline product is isolated by filtration with suction. This gives 21.5 g (52% of theory) of 4-methoxycarbonyl-2-methyl-thiophene-3-sulphonamide.

Analogously to Example (II-1), it is also possible to prepare, for example, the following compounds of the general formula (II):
4-ethoxycarbonyl-2-methyl-thiophene-3-sulphonamide,
4-n-propoxycarbonyl-2-methyl-thiophene-3-sulphonamide,
4-i-propoxycarbonyl-2-methyl-thiophene-3-sulphonamide,
4-methoxycarbonyl-2-ethyl-thiophene-3-sulphonamide,
4-ethoxycarbonyl-2-ethyl-thiophene-3-sulphonamide,
4-n-propoxycarbonyl-2-ethyl-thiophene-3-sulphonamide,
4-i-propoxycarbonyl-2-ethyl-thiophene-3-sulphonamide,
4-methoxycarbonyl-2-n-propyl-thiophene-3-sulphonamide,
4-ethoxycarbonyl-2-n-propyl-thiophene-3-sulphonamide,
4-n-propoxycarbonyl-2-n-propyl-thiophene-3-sulphonamide,
4-i-propoxycarbonyl-2-n-propyl-thiophene-3-sulphonamide,
4-methoxycarbonyl-2-i-propyl-thiophene-3-sulphonamide,
4-ethoxycarbonyl-2-i-propyl-thiophene-3-sulphonamide,
4-n-propoxycarbonyl-2-i-propyl-thiophene-3-sulphonamide,
4-i-propoxycarbonyl-2-i-propyl-thiophene-3-sulphonamide.

Starting Materials of the Formula (VI)

Example (VI-1)

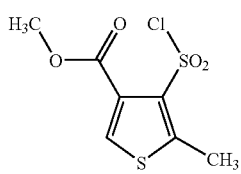

At from 0° C. to 5° C., a solution of 19.9 g (0.29 mol) of sodium nitrite in 60 ml of water is added dropwise with stirring to a solution of 42.7 g (0.25 mol) of methyl 3-amino-2-methyl-thiophene-4-carboxylate in 75 ml of 10% strength aqueous hydrochloric acid. The reaction mixture is stirred at from 0° C. to 5° C. for 60 minutes. The excess of nitride is then destroyed using amidosulphonic acid. At from 0° C. to 5° C., the mixture is then added dropwise with stirring to a solution of 35 g (0.55 mol) of sulphur dioxide in 300 ml of methylene chloride. After addition of 1.5 g of copper(I) chloride and 1.5 g of dodecyl-trimethylammonium bromide, the reaction mixture is stirred at 40° C. for 60 minutes and then at 20° C. for 12 hours. 18 ml of 35% strength aqueous hydrochloric acid are then added, the mixture is stirred at 20° C. for 4 hours and the phases are then separated. The aqueous phase is re-extracted with methylene chloride and the combined organic phases are washed with water, dried with magnesium sulphate and filtered. The filtrate is concentrated under water pump vacuum and the residue is crystallized from hexane.

This gives 51.7 g (81% of theory) of 4-methoxycarbonyl-2-methyl-thiophene-3-sulphonyl chloride.

Analogously to Example (VI-1), it is also possible to prepare, for example, the following compounds of the formula (VI):
4-ethoxycarbonyl-2-methyl-thiophene-3-sulphonyl chloride,
4-n-propoxycarbonyl-2-methyl-thiophene-3-sulphonyl chloride,
4-i-propoxycarbonyl-2-methyl-thiophene-3-sulphonyl chloride,
4-methoxycarbonyl-2-ethyl-thiophene-3-sulphonyl chloride,
4-ethoxycarbonyl-2-ethyl-thiophene-3-sulphonyl chloride,
4-n-propoxycarbonyl-2-ethyl-thiophene-3-sulphonyl chloride,
4-i-propoxycarbonyl-2-ethyl-thiophene-3-sulphonyl chloride,
4-methoxycarbonyl-2-n-propyl-thiophene-3-sulphonyl chloride,
4-ethoxycarbonyl-2-n-propyl-thiophene-3-sulphonyl chloride,
4-n-propoxycarbonyl-2-n-propyl-thiophene-3-sulphonyl chloride,
4-i-propoxycarbonyl-2-n-propyl-thiophene-3-sulphonyl chloride,
4-methoxycarbonyl-2-i-propyl-thiophene-3-sulphonyl chloride,
4-ethoxycarbonyl-2-i-propyl-thiophene-3-sulphonyl chloride,
4-n-propoxycarbonyl-2-i-propyl-thiophene-3-sulphonyl chloride,
4-i-propoxycarbonyl-2-i-propyl-thiophene-3-sulphonyl chloride.

Starting Materials of the Formula (X)

Example (X-1)

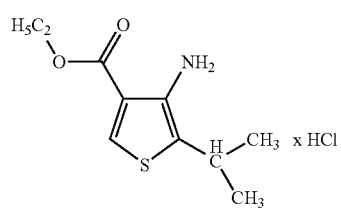

Step 1

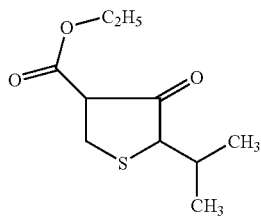

Under water pump vacuum, 61 g of a 20% strength solution of sodium ethoxide in ethanol (213 mmol of NaOCH$_3$) are evaporated to dryness. The residue is taken up in 80 ml of toluene, and 28.6 g (109 mmol) of ethyl 2-(2-ethoxycarbonyl-ethylthio)-3-methyl-butyrate are then added and the reaction mixture is stirred at from 70° C. to 80° C. for 12 hours. After cooling to room temperature, the mixture is poured into ice-water and then acidified with conc. hydrochloric acid. The organic phase is then separated off, the aqueous phase is re-extracted with diethyl ether and the organic phases are combined, dried with magnesium sulphate and filtered. The filtrate is concentrated under water pump vacuum and the residue is purified by distillation under reduced pressure.

This gives 22.6 g (96% of theory) of ethyl 5-i-propyl-4-oxo-tetrahydrothiophene-3-carboxylate of boiling point 115° C. (at 0.5 mbar).

Step 2

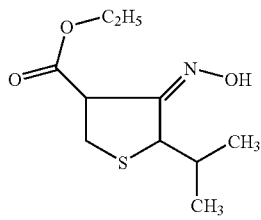

A mixture of 38 g (176 mmol) of ethyl 5-i-propyl-4-oxo-tetrahydrothiophene-3-carboxylate, 35 g of hydroxylamine hydrochloride, 53 g of barium carbonate and 300 ml of ethanol is heated under reflux for 12 hours and then filtered whilst still hot. The filtrate is concentrated under water pump vacuum, and the residue is taken up in diethyl ether, washed with water, dried with magnesium sulphate and filtered. From the filtrate, the solvent is carefully distilled off under reduced pressure.

This give 34.2 g (86% of theory) of ethyl 4-hydroximino-5-i-propyl-dihyro-5H-thiophene-3-carboxylate as an oil which can be reacted further without any further purification.

Step 3

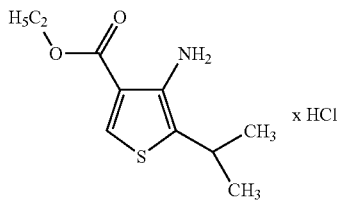

33 g (143 mmol) of ethyl 4-hydroximino-5-i-propyl-dihydro-5H-thiophene-3-carboxylate are dissolved in 250 ml of diethyl ether and, with ice-cooling, hydrogen chloride is introduced for 20 minutes (until saturation has been reached). The mixture is allowed to stand at room temperature (about 20° C.) for 2 days and then concentrated under water pump vacuum, and the residue is crystallized from acetone.

This gives 13 g (37% of theory) of ethyl 4-amino-5-i-propyl-thiophene-3-carboxylate hydrochloride as a solid product.

Example (X-2)

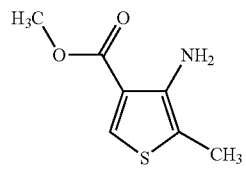

Step 1

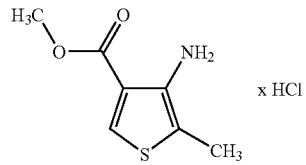

A mixture of 310 g (1.78 mol) of methyl 5-methyl-4-oxo-tetrahydrothiophene-3-carboxylate, 155 g (2.27 mol) of hydroxylamine hydrochloride and 900 ml of acetonitrile is heated under reflux for 60 minutes. After cooling to room temperature (about 20° C.), the resulting crystalline product is isolated by filtration with suction.

This gives 335 g (91% of theory) of methyl 4-amino-5-methyl-thiophene-3-carboxylate hydrochloride of melting point 132° C.

Step 2

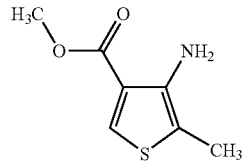

273 g (1.62 mol) of methyl 4-amino-5-methyl-thiophene-3-carboxylate hydrochloride are dissolved in 1 liter of water, and 2 liters of methylene chloride are added below the layer of water. With vigorous stirring, 125 g of sodium bicarbonate are then added, and the mixture is stirred for another 15 minutes. The organic phase is separated off, dried with magnesium sulphate and filtered. The filtrate is concentrated under water pump vacuum, the residue is digested with petroleum ether and the crystalline product is isolated by filtration with suction.

This gives 148 g (53% of theory) of methyl 4-amino-5-methyl-thiophene-3-carboxylate of melting point 78° C.

Analogously to Examples (X-1) and (X-2), it is also possible to prepare, for example, the following compounds of the general formula (X):
ethyl 4-amino-5-methyl-thiophene-3-carboxylate
(m.p.: 50° C., hydrochloride: m.p.: 143° C.), n-propyl 4-amino-5-methyl-thiophene-3-carboxylate,
i-propyl 4-amino-5-methyl-thiophene-3-carboxylate,
methyl 4-amino-5-ethyl-thiophene-3-carboxylate,
ethyl 4-amino-5-ethyl-thiophene-3-carboxylate,
n-propyl 4-amino-5-ethyl-thiophene-3-carboxylate,
(oil, hydrochloride: m.p.: 140° C.),
i-propyl 4-amino-5-ethyl-thiophene-3-carboxylate,
(oil, hydrochloride: m.p.: 142° C.),
methyl 4-amino-5-n-propyl-thiophene-3-carboxylate,
ethyl 4-amino-5-n-propyl-thiophene-3-carboxylate,
n-propyl 4-amino-5-n-propyl-thiophene-3-carboxylate,
i-propyl 4-amino-5-n-propyl-thiophene-3-carboxylate,
methyl 4-amino-5-i-propyl-thiophene-3-carboxylate,
n-propyl 4-amino-5-i-propyl-thiophene-3-carboxylate,
i-propyl 4-amino-5-i-propyl-thiophene-3-carboxylate, and in each case the corresponding hydrochlorides.

Use Examples

Example A

Pre-Emergence Test

| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 liters of water per hectare.

After three weeks, the degree of damage to the plants is rated in % damage in comparison to the development of the untreated control.

The figure denote:

0%=no effect (like untreated control)

100%=total destruction

In this test, for example, the compounds of Preparation Examples 1, 2, 3, 4, 5, 6, 7, 8, 9, 10, 11 and 12 exhibit very strong activity against weeds, and some of them are tolerated well by crop plants, such as, for example, cotton, maize and wheat.

TABLE A1

Pre-emergence test/greenhouse

| Active compound of Preparation Example No. | Application rate (g of ai/ha) | Alopecurus | Cyperus | Setaria | Abutilon | Amaranthus | Galium | Sinapis | Xanthium |
|---|---|---|---|---|---|---|---|---|---|
| (2) | 60 | 95 | 100 | 95 | 95 | 100 | — | 95 | 100 |
| (5) | 250 | 99 | 100 | 100 | 95 | 100 | 95 | 95 | 99 |
| (6) | 250 | 95 | 100 | 100 | 100 | 95 | 90 | 95 | 95 |
| (7) | 250 | 90 | 100 | 95 | 95 | 95 | 95 | 95 | — |
| (9) | 250 | 95 | 100 | 100 | 100 | 100 | 95 | 95 | — |
| (10) | 250 | 95 | 95 | 100 | 95 | 100 | 95 | 100 | 90 |

TABLE A2

Pre-emergence test/greenhouse

| Active compound of Preparation Example No. | Application rate (g of ai/ha) | Alopecurus | Bromus | Setaria | Chenopodium | Matricaria | Stellaria | Veronica | Viola |
|---|---|---|---|---|---|---|---|---|---|
| (1) | 60 | 90 | 90 | 90 | 100 | 95 | 95 | 100 | 100 |

TABLE A3

Pre-emergence test/greenhouse

| Active compound of Preparation Example No. | Application rate (g of ai/ha) | Wheat | Barley | Alopecurus | Amaranthus | Solanum | Stellaria |
|---|---|---|---|---|---|---|---|
| (3) | 60 | 0 | 0 | 80 | 95 | 90 | 95 |

TABLE A4

Pre-emergence test/greenhouse

| Active compound of Preparation Example No. | Application rate (g of ai/ha) | Wheat | Bromus | Cyperus | Echinochloa | Solanum | Stellaria | Veronica | Viola |
|---|---|---|---|---|---|---|---|---|---|
| (4) | 125 | 20 | 100 | 100 | 100 | 100 | 100 | 100 | 100 |

TABLE A5

Pre-emergence test/greenhouse

| Active compound of Preparation Example No. | Application rate (g of ai/ha) | Cotton | Bromus | Echinochloa | Chenopodium | Solanum | Stellaria | Veronica | Viola |
|---|---|---|---|---|---|---|---|---|---|
| (8) | 60 | 0 | 90 | 90 | 90 | 90 | 95 | 95 | 100 |

TABLE A6

Pre-emergence test/greenhouse

| Active compound of Preparation Example No. | Application rate (g of ai/ha) | Maize | Alopecurus | Digitaria | Setaria | Amaranthus | Chenopodium | Matricaria | Solanum |
|---|---|---|---|---|---|---|---|---|---|
| (11) | 60 | 10 | 100 | 100 | 100 | 100 | 100 | 100 | 100 |

TABLE A7

Pre-emergence test/greenhouse

| Active compound of Preparation Example No. | Application rate (g of ai/ha) | Maize | Bromus | Cyperus | Setaria | Abutilon | Stellaria | Veronica | Viola |
|---|---|---|---|---|---|---|---|---|---|
| (12) | 60 | 10 | 100 | 100 | 100 | 100 | 100 | 100 | 100 |

Example B

Post-Emergence Test

| | |
|---|---|
| Solvent: | 5 parts by weight of acetone |
| Emulsifier: | 1 part by weight of alkylaryl polyglycol ether |

To produce a suitable preparation of active compound, one part by weight of active compound is mixed with the stated amount of solvent, the stated amount of emulsifier is added and the concentrate is diluted with water to the desired concentration.

Test plants which have a height of 5-15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

In this test, for example, the compounds of Preparation Examples 1, 2, 3, 4, 5, 6, 7, 8, 9, 10, 11 and 12 exhibit very strong activity against weeds, and some of them are tolerated well by crop plants, such as, for example, barley and wheat.

TABLE B1

Post-emergence test/greenhouse

| Active compound of Preparation Example No. | Application rate (g of ai/ha) | Wheat | Alopecurus | Echinochloa | Abutilon | Amaranthus | Matricaria | Solanum | Stellaria |
|---|---|---|---|---|---|---|---|---|---|
| (3) | 15 | 0 | 70 | 60 | 95 | 95 | 90 | 95 | 100 |

TABLE B2

| | | Post-emergence test/greenhouse | | | | | | |
|---|---|---|---|---|---|---|---|---|
| Active compound of Preparation Example No. | Application rate (g of ai/ha) | Wheat | Abutilon | Amaranthus | Ipomoea | Matricaria | Solanum | Stellaria |
| (4) | 8 | 10 | 95 | 95 | 95 | 90 | 95 | 95 |

TABLE B3

| | | Post-emergence test/greenhouse | | | | | | | |
|---|---|---|---|---|---|---|---|---|---|
| Active compound of Preparation Example No. | Application rate (g of ai/ha) | Barley | Wheat | Echinochloa | Amaranthus | Chenopodium | Stellaria | Veronica | Viola |
| (5) | 2 | 10 | 10 | 95 | 99 | 95 | 100 | 90 | 90 |

TABLE B4

| | | Post-emergence test/greenhouse | | | | | | |
|---|---|---|---|---|---|---|---|---|
| Active compound of Preparation Example No. | Application rate (g of ai/ha) | Wheat | Maize | Setaria | Abutilon | Amaranthus | Solanum | Stellaria |
| (10) | 15 | 10 | 10 | 95 | 90 | 90 | 90 | 95 |

TABLE B5

| | | Post-emergence test/greenhouse | | | | | | |
|---|---|---|---|---|---|---|---|---|
| Active compound of Preparation Example No. | Application rate (g of ai/ha) | Alopecurus | Avenafatua | Setaria | Abutilon | Amaranthus | Sinapis | Xanthium |
| (2) | 60 | 95 | 80 | 100 | 100 | 100 | 100 | 100 |
| (1) | 250 | 100 | 100 | 100 | 100 | 100 | 100 | 100 |
| (6) | 250 | 100 | 100 | 100 | 100 | 100 | 100 | 100 |
| (7) | 250 | 95 | 100 | 90 | 100 | 100 | 100 | 90 |
| (8) | 250 | 100 | 100 | 100 | 100 | 100 | 95 | 100 |
| (9) | 250 | 100 | 100 | 100 | 100 | 100 | 100 | 100 |
| (11) | 250 | 100 | 100 | 100 | 100 | 100 | 100 | 100 |
| (12) | 250 | 95 | 100 | 100 | 100 | 100 | 100 | 100 |

What is claimed is:

1. A process for preparing a compound of formula (I) or salts thereof:

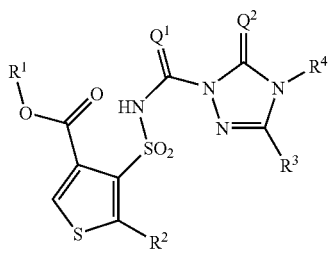

in which
Q$^1$ represents O,
Q$^2$ represents O,
R$^1$ represents —CH$_3$,
R$^2$ represents —CH$_3$,
R$^3$ represents —OCH$_3$, and
R$^4$ represents —CH$_3$,
the process comprising:

(b) reacting a substituted thien-3-yl-sulphonyl iso(thio)cyanates of the general formula (IV)

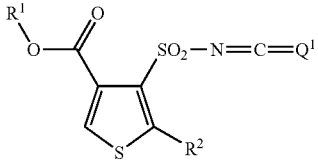

in which
Q$^1$, R$^1$ and R$^2$ are each as defined above,
with triazolin(ethi)ones of the formula (V)

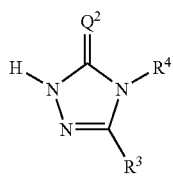

in which
Q$^2$, R$^3$ and R$^4$ are each as defined above, if appropriate in the presence of a reaction auxiliary and if appropriate in the presence of a diluent,
or
(c) reacting a substituted thiophene-3-sulphonyl chlorides of the formula (VI)

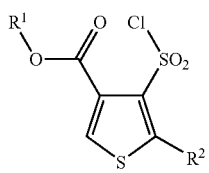
(VI)

in which
R$^1$ and R$^2$ are each as defined above,
with triazolin(ethi)ones of the formula (V)

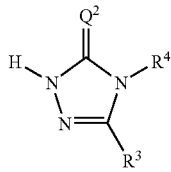
(V)

in which
Q$^2$, R$^3$ and R$^4$ are each as defined above,
and metal (thio)cyanates of the formula (VII)

M-Q$^1$-CN   (VII)

in which
Q$^1$ is as defined above,
if appropriate in the presence of a reaction auxiliary and if appropriate in the presence of a diluent,
or
(d) reacting substituted thiophene-3-sulphonyl chlorides of the formula (VI)

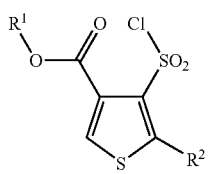
(VI)

in which
R$^1$ and R$^2$ are each as defined above,
with triazolin(ethi)one-(thio)carboxamides of the formula (VIII)

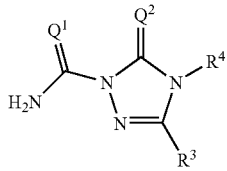
(VIII)

in which
Q$^1$, Q$^2$, R$^3$ and R$^4$ are each as defined above,
if appropriate in the presence of a reaction auxiliary and if appropriate in the presence of a diluent,
or
(e) reacting substituted thien-3-yl-sulphonylamino(thio)carbonyl compounds of the formula (IX)

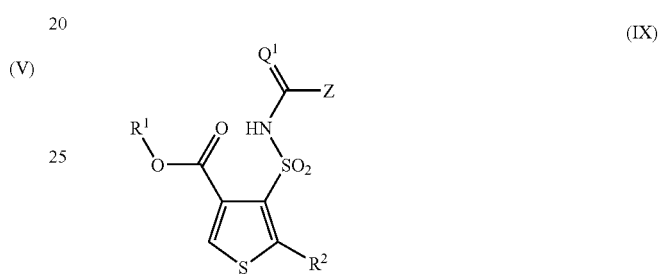
(IX)

in which
Q$^1$, R$^1$ and R$^2$ are each as defined above, and
Z represents halogen, alkoxy, aryloxy or arylalkoxy,
with triazolin(ethi)ones of the formula (V)

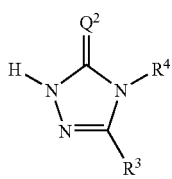
(V)

in which
Q$^2$, R$^3$ and R$^4$ are each as defined in above,
if appropriate in the presence of a reaction auxiliary and if appropriate in the presence of a diluent.

2. The process of claim 1, wherein the salts are selected from sodium, potassium, magnesium, calcium, ammonium, $C_1$-$C_4$-alkyl-ammonium, di-($C_1$-$C_4$-alkyl)-ammonium, tri-($C_1$-$C_4$-alkyl)-ammonium, tetra-($C_1$-$C_4$-alkyl)-ammonium, tri-($C_1$-$C_4$-alkyl)-sulphonium, $C_5$- or $C_6$-cycloalkyl-ammonium or di-($C_1$-$C_2$-alkyl)-benzylammonium.

* * * * *